(12) United States Patent
Maibach et al.

(10) Patent No.: US 7,205,003 B2
(45) Date of Patent: Apr. 17, 2007

(54) METHOD AND TOPICAL FORMULATION FOR TREATING SKIN CONDITIONS ASSOCIATED WITH AGING

(75) Inventors: Howard I. Maibach, San Francisco, CA (US); Eric C. Luo, Plano, TX (US); Tsung-Min Hsu, San Diego, CA (US)

(73) Assignee: Dermatrends, Inc., Minneapolis, MN (US)

( * ) Notice: Subject to any disclaimer, the term of this patent is extended or adjusted under 35 U.S.C. 154(b) by 0 days.

(21) Appl. No.: 10/252,784

(22) Filed: Sep. 23, 2002

(65) Prior Publication Data

US 2003/0099678 A1    May 29, 2003

Related U.S. Application Data

(63) Continuation-in-part of application No. 09/962,622, filed on Sep. 24, 2001, now abandoned.

(51) Int. Cl.
*A61K 6/00* (2006.01)
*A61K 7/00* (2006.01)
*A61K 33/00* (2006.01)
*A61K 59/00* (2006.01)

(52) U.S. Cl. ...................... 424/722; 424/401
(58) Field of Classification Search ............... 424/665, 424/680, 722, 401
See application file for complete search history.

(56) References Cited

U.S. PATENT DOCUMENTS

| | | | |
|---|---|---|---|
| 4,355,020 A | 10/1982 | Kuy | |
| 5,037,648 A | 8/1991 | Joiner | |
| 5,169,967 A | 12/1992 | Assmus et al. | |
| 5,462,744 A | 10/1995 | Gupte et al. | |
| 5,492,894 A * | 2/1996 | Bascom et al. | 514/18 |
| 5,641,813 A | 6/1997 | Franklin et al. | |
| 5,773,034 A | 6/1998 | Camprasse et al. | |
| 5,786,381 A | 7/1998 | Franklin et al. | |
| 5,837,735 A * | 11/1998 | Miyata et al. | 514/605 |
| 5,851,556 A | 12/1998 | Breton et al. | |
| 5,900,257 A | 5/1999 | Breton et al. | |
| 5,928,658 A | 7/1999 | Kishida et al. | |
| 6,001,367 A | 12/1999 | Bazin et al. | |
| 6,063,406 A | 5/2000 | Hornack | |
| 6,190,677 B1 | 2/2001 | Remy | |
| 6,287,553 B1 | 9/2001 | Alaluf et al. | |

FOREIGN PATENT DOCUMENTS

| | | |
|---|---|---|
| EP | 0842662 A1 | 5/1998 |
| EP | 0965327 A1 | 12/1999 |
| JP | 02019311 | 1/1990 |
| JP | 11269303 | 10/1999 |
| JP | 2002212052 | 7/2002 |
| JP | 2002234845 | 8/2002 |
| JP | 2002326922 | 11/2002 |
| WO | WO 01/43775 | 6/2001 |

* cited by examiner

*Primary Examiner*—Sreenivasan Padmanabhan
*Assistant Examiner*—Jennifer Kim
(74) *Attorney, Agent, or Firm*—Fredrikson & Byron, PA

(57) ABSTRACT

A composition and method are provided for alleviating the dermatological signs of intrinsic and extrinsic aging. A topical formulation containing a cosmeceutically active base, wherein the formulation provides a pH in the range of about 8.0 to 13.0 at the skin surface, is applied to the skin in order to prevent or treat aging-related skin conditions such as wrinkles, dry skin, age spots, sun damage (particularly UV radiation-induced oxidative stress), blemishes, hyperpigmented skin, age spots, increased skin thickness, loss of skin elasticity and collagen content, dry skin, lentigines and melasmas. The cosmeceutically active base is either an inorganic base, such as an inorganic hydroxide, an inorganic oxide, or a metal salt of a weak acid, or an organic base, particularly a nitrogenous base such as may be selected from primary amines, secondary amines, tertiary amines, amides, oximes, nitrites, aromatic and non-aromatic nitrogen-containing heterocycles, urea, and mixtures thereof.

11 Claims, 3 Drawing Sheets

METHOD AND TOPICAL FORMULATION FOR TREATING SKIN CONDITIONS ASSOCIATED WITH AGING

CROSS-REFERENCE TO RELATED APPLICATIONS

This application is a continuation-in-part of U.S. Ser. No. 09/962,622, filed Sep. 24, 2001 now abandoned, which is hereby incorporated by reference.

TECHNICAL FIELD

This application relates to compositions and methods for alleviating the dermatological signs of aging, including changes or damage to skin associated with intrinsic aging, as well as changes or damage caused by extrinsic factors such as sunlight, radiation, air pollution, wind, cold, heat, dampness, chemicals, and cigarette smoking.

BACKGROUND

Human skin is a structurally complex, relatively thick membrane comprised of two principal components, the outer epidermis and the underlying dermis, which is situated above the subcutaneous adipose or fat tissues.

The epidermis consists of four distinct layers, the stratum corneum, stratum granulosum, stratum spinosum, and stratum basale. In the skin of palms and soles only, there is normally one additional zone called the stratum lucidum between the stratum corneum and the stratum granulosum.

The dermis is comprised mainly of collagen, elastic fibers, glycosaminoglycans, and proteoglycans including hyaluronic acid, dermatan sulfate, and chondroitin sulfate, formerly known as mucopolysaccharides. Fibroblasts, the predominant cells of the dermis, synthesize collagen, elastic fibers, proteoglycans, and glycosaminoglycans. Collagen makes up approximately 77%, elastic fibers account for about 2%, and glycosaminoglycans constitute around 0.2% of the dry weight of the dermis. Collagen provides the tensile strength of and elastic fibers give resilience to the dermis. The glycosaminoglycans bind water to form a gelatinous mass between collagen and elastic fibers, which acts as a lubricant and shock absorber for the dermis during movement of the skin.

Cutaneous aging, while having epidermal concomitants, primarily involves dermal and subcutaneous changes, and is caused by (a) internal factors alone, as in intrinsic aging and (b) external factors, as in extrinsic aging. Intrinsic aging is also known as natural or chronologic aging, and extrinsic aging is often called photoaging. "Photodamage" implies skin damage caused by chronic sun exposure. These terms may be described as follows.

Intrinsic aging of skin, in sun-protected skin of the upper arm and abdomen, is an inherent degenerative process due to declining physiologic functions and capacities. Such aging process may include qualitative and quantitative skin changes and includes diminished or defective synthesis of collagen and elastic fibers, and proteoglycans and glycosaminoglycans in the dermis. Signs of intrinsic aging include progressive thinning of skin, deepening of skin lines and fine wrinkles, lusterless skin surface, and loss of skin elasticity and recoilability. Although intrinsic aging of living creatures is neither reversible nor preventable, modification and improvement of skin signs associated with such aging process can be achieved through topical management.

Extrinsic aging of skin is a distinctive process caused by external factors, which include sunlight, radiation, air pollution, wind, cold, dampness, heat, and chemicals.

Photoaging of skin may be defined as destructive cutaneous changes caused by chronic exposure to sunlight. Signs of photoaging on the face and back of hands include coarse and deepened wrinkles due to changes and degeneration of collagen and elastic fibers; marked loss of elasticity and recoilability; leathery skin surface and skin lesions with abnormal pigmentation and increased numbers of age spots, pigmented spots, blotches and nodules. Histologically, the qualities and quantities of elastin and collagen tissues are changed. Normal elastin in tissues is replaced by abnormal elastin characterized as solar elastosis, and the normal collagen fibers are decreased.

Photodamage of skin, also called solar damage, may be defined as cutaneous damage caused by chronic exposure to solar radiation and is associated with development of neoplastic lesions. Skin disorders caused by photodamage include pre-malignant lesions, basal cell carcinomas, squamous cell carcinomas, and malignant melanomas.

The intact skin of humans is an effective barrier to many natural and synthetic substances. Many cosmetic and pharmaceutical agents, which are pharmacologically effective on oral or systemic administration, may be much less effective or even totally ineffective, when applied topically to the skin. Therefore, there is an ongoing need in the art for new and effective regimens for treating aging-related skin conditions. The present invention addresses these and other needs in the art by providing novel methods and topical formulations for treating a variety of aging-related skin conditions, including wrinkles, age spots, sun damage (particularly UV radiation-induced oxidative stress), blemishes, hyperpigmented skin, age spots, increased skin thickness, loss of skin elasticity and collagen content, dry skin, lentigines, and melasmas. Treatment is effected by topical application of a cosmeceutically active base, a surprisingly effective yet simple means for treating aging-related skin conditions. To the best of applicants' knowledge, the use of cosmeceutically active bases as disclosed herein has not been suggested in the art and represents a significant and unexpected advance in the art.

SUMMARY OF THE INVENTION

It is thus a primary object of the invention address the above-discussed needs in the art by providing a novel method of treating an aging-related skin condition.

It is another object of the invention to provide such a method wherein the aging-related skin condition is treated by topically administering to an individual's skin a formulation containing a cosmeceutically acceptable base.

It is still another object of the invention to provide such a method wherein the cosmeceutically acceptable base is present at a concentration effective to provide a pH within the range of approximately 8.0 to 13.0 at the skin surface.

It is yet another object of the invention to provide such a method wherein the cosmeceutically acceptable base is an inorganic base, e.g., an inorganic hydroxide, an inorganic oxide, an inorganic salt of a weak acid, or a combination thereof.

It is a further object of the invention to provide such a method wherein the cosmeceutically acceptable base is an organic base, particularly a nitrogenous base.

It is still a further object of the invention to provide a topical formulation for carrying out the aforementioned methods, the formulation containing a cosmeceutically active agent consisting essentially of a cosmeceutically acceptable base present at a concentration sufficient to provide a pH within the range of approximately 8.0 to 13.0 at the region of the skin to which the formulation is applied It is an additional object of the invention to provide such a formulation, wherein the formulation further contains at least one cosmeceutically acceptable excipient and/or at least one cosmeceutically acceptable carrier.

Additional objects, advantages, and novel features of the invention will be set forth in the description that follows, and in part will become apparent to those skilled in the art upon examination of the following, or may be learned by practice of the invention.

DETAILED DESCRIPTION OF THE INVENTION

I. Definitions and Nomenclature

Figure 1:
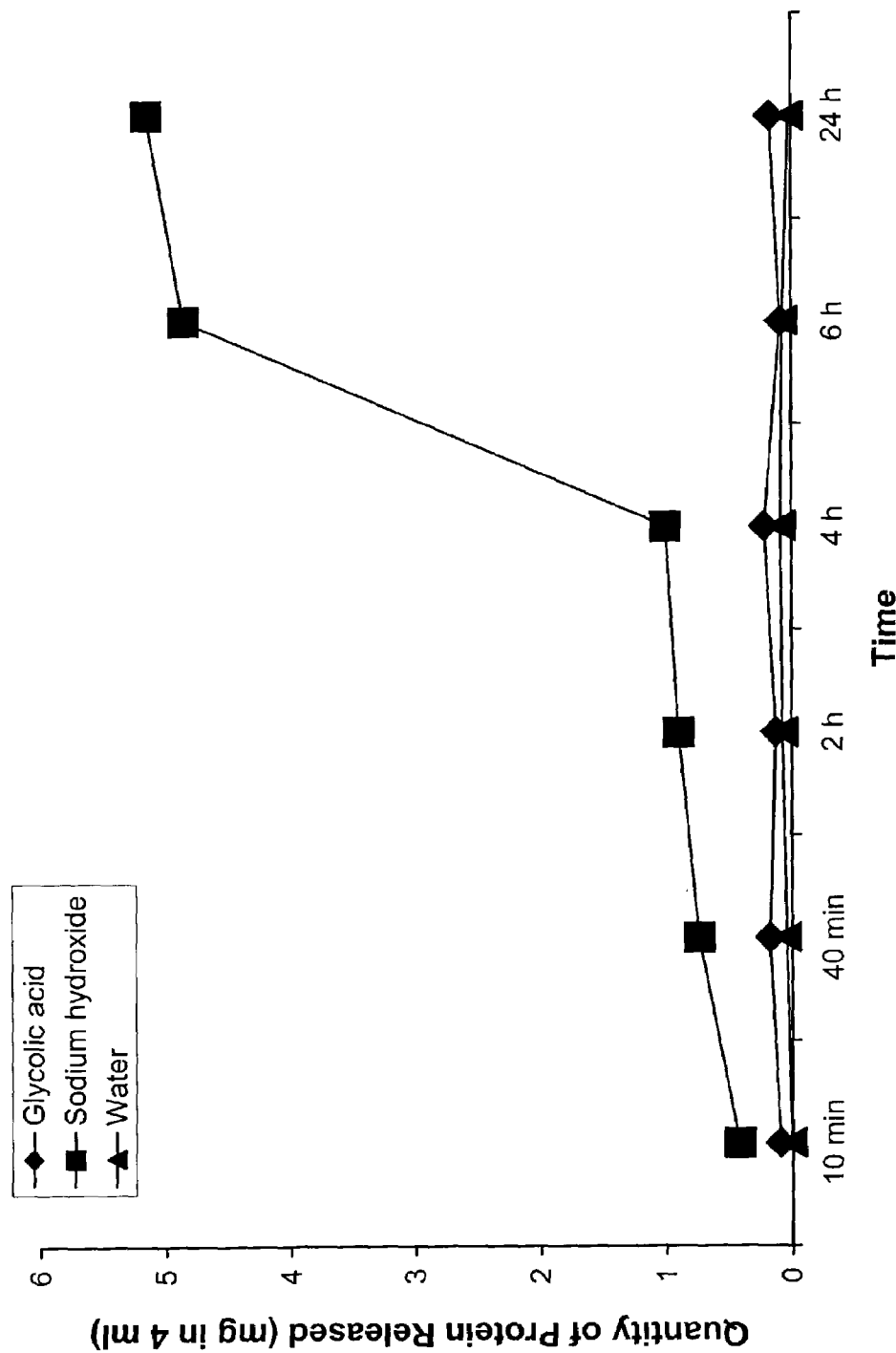
FIG. 1 is a graph comparing the in vitro release of protein from the stratum corneum upon incubation in a 0.05 M sodium hydroxide solution with that observed upon incubation in a glycolic acid solution, as described in Example 1. As explained in Example 1, the experiment involved periodic evaluation over a 24-hour time period.

Before describing the present invention in detail, it is to be understood that this invention is not limited to particular formulation types, formulation components, manufacturing methods, or the like, as such may vary. It is also to be understood that the terminology used herein is for the purpose of describing particular embodiments only, and is not intended to be limiting.

It must be noted that, as used in this specification and the appended claims, the singular forms "a," "an," and "the" include plural referents unless the context clearly dictates otherwise. Thus, for example, "a cosmeceutically active base" refers not only to a single such base but also to a mixture of two or more cosmeceutically active bases, reference to "a vehicle" or "a carrier" includes a single vehicle or a single carrier as well as mixtures of two or more vehicles or carriers, and the like.

In describing and claiming the present invention, the following terminology will be used in accordance with the definitions set out below.

The terms "treating" and "treatment" as used herein refer to reduction in severity and/or elimination of skin related conditions resulting from intrinsic and/or extrinsic aging processes of the skin. The present method of "treating" a skin condition related to aging, as the term is used herein, refers to the prevention of aging-related skin conditions as well as the treatment of aging-related skin conditions in affected individuals.

The term "aging-related skin condition" relates to any skin condition or disorder associated with, caused by, or affected by, intrinsic aging and/or extrinsic aging. Aging-related skin conditions that may be treated using the present methods and formulations include, but are not limited to, wrinkles, age spots, sun damage (particularly UV radiation-induced oxidative stress), blemishes, hyperpigmented skin, age spots, increased skin thickness, loss of skin elasticity and collagen content, dry skin, lentigines, and melasmas.

By "cosmeceutically effective" is meant a nontoxic agent that has medicinal or drug-like properties which, when applied to the surface of skin, beneficially affects the biological functioning of that skin.

The terms "cosmeceutically active agent" and "cosmeceutically active base" are used interchangeably herein to refer to a cosmeceutically effective basic compound or composition of matter which, when topically administered to a human patient, is effective to treat one or more aging-related skin conditions as defined above. Also included are derivatives and analogs of those compounds or classes of compounds specifically mentioned that also induce the desired effect, i.e., treatment of an aging-related skin condition.

By "cosmeceutically acceptable," such as in the recitation of a "cosmeceutically acceptable carrier," or a "cosmeceutically acceptable derivative," is meant a compound that is not biologically or otherwise undesirable, i.e., the compound may be incorporated into a cosmeceutical formulation of the invention and topically administered to a patient without causing any undesirable biological effects or interacting in a deleterious manner with any of the other components of the cosmeceutical formulation in which it is contained. The term "pharmaceutically acceptable" is used in an analogous manner, to refer to a compound or composition that may be incorporated into a pharmaceutical formulation herein (i.e., a cosmeceutical formulation containing one or more pharmacologically active agents) without causing undesirable biological effects or unwanted interaction with other components of the formulation.

The term "base" is used in its traditional sense, i.e., a substance that dissolves in water to produce hydroxide ions. The water is typically an aqueous fluid, and may be natural moisture at the skin surface. Similarly, any liquid or semi-solid formulation that is used is preferably aqueous or used in conjunction with an overlayer of an occlusive material. Any base may be used provided that the compound provides free hydroxide ions in the presence of an aqueous fluid. Bases can provide free hydroxide ions either directly or indirectly and thus can also be referred to as "hydroxide-releasing agents". Hydroxide-releasing agents that provide free hydroxide ions directly typically contain hydroxide groups and release the hydroxide ions directly into solution, for example, alkali metal hydroxides. Hydroxide-releasing agents that provide free hydroxide ions indirectly are typically those compounds that are acted upon chemically in an aqueous environment and the reaction produces hydroxide ions, for example metal carbonates or amines.

The term "active agent" is used herein to refer to a chemical material or compound that induces a desired beneficial effect when administered topically, and include agents that are therapeutically and/or prophylactically effective as pharmaceuticals ("pharmacologically active agents"), as well as agents that are cosmeceutically effective ("cosmeceutically active agents"). Also included are derivatives and analogs of those compounds or classes of compounds specifically mentioned that also induce the desired effect. Topical pharmacologically active agents are optionally incorporated into the present cosmeceutical formulations. By an "effective" amount of an active agent is meant a nontoxic but sufficient amount of an active agent to provide the desired beneficial effect. More specifically, by a "therapeutically effective," "prophylactically effective," or "cosmeceutically effective" amount is meant a nontoxic but sufficient amount of a beneficial agent to provide the desired therapeutic, prophylactic, or cosmeceutical effect.

The term "topical administration" is used in its conventional sense to mean topical application of a formulation to the skin.

"Carriers" or "vehicles" as used herein refer to carrier materials suitable for incorporation in a topically applied composition. Carriers and vehicles useful herein include any such materials known in the art, which are nontoxic and do not interact with other components of the formulation in which it is contained in a deleterious manner.

The term "aqueous" refers to a formulation that contains water or that becomes water-containing following application to the skin or mucosal tissue.

In describing molecular structures and formulae herein, the phrase "having the formula" or "having the structure" is not intended to be limiting and is used in the same way that the term "comprising" is commonly used.

The term "alkyl" as used herein refers to a branched or unbranched saturated hydrocarbon group typically although not necessarily containing 1 to about 24 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl, and the like. Generally, although again not necessarily, alkyl groups herein contain 1 to about 12 carbon atoms. The term "lower alkyl" intends an alkyl group of one to six carbon atoms, preferably one to four carbon atoms. "Substituted alkyl" refers to alkyl substituted with one or more substituent groups, and the terms "heteroatom-containing alkyl" and "heteroalkyl" refer to alkyl in which at least one carbon atom is replaced with a heteroatom. If not otherwise indicated, the terms "alkyl" and "lower alkyl" include linear, branched, cyclic, unsubstituted, substituted, and/or heteroatom-containing alkyl or lower alkyl.

The term "alkenyl" as used herein refers to a branched or unbranched hydrocarbon group typically although not necessarily containing 2 to about 24 carbon atoms and at least one double bond, such as ethenyl, n-propenyl, isopropenyl, n-butenyl, isobutenyl, octenyl, decenyl, and the like. Generally, although again not necessarily, alkenyl groups herein contain 2 to about 12 carbon atoms. The term "lower alkenyl" intends an alkenyl group of two to six carbon atoms, preferably two to four carbon atoms. "Substituted alkenyl" refers to alkenyl substituted with one or more substituent groups, and the terms "heteroatom-containing alkenyl" and "heteroalkenyl" refer to alkenyl in which at least one carbon atom is replaced with a heteroatom.

The term "aryl" as used herein, and unless otherwise specified, refers to an aromatic substituent containing a single aromatic ring or multiple aromatic rings that are fused together, linked covalently, or linked to a common group such as a methylene or ethylene moiety. The common linking group may also be a carbonyl as in benzophenone, an oxygen atom as in diphenylether, or a nitrogen atom as in diphenylamine. Preferred aryl groups contain one aromatic ring and are referred to as "monocyclic aryl." "Substituted aryl" refers to an aryl moiety substituted with one or more substituent groups, and the terms "heteroatom-containing aryl" and "heteroaryl" refer to aryl in which at least one carbon atom is replaced with a heteroatom.

The term "heteroatom-containing" as in a "heteroatom-containing hydrocarbyl group" refers to a molecule or molecular fragment in which one or more carbon atoms is replaced with an atom other than carbon, e.g., nitrogen, oxygen, sulfur, phosphorus or silicon. Similarly, the term "heteroalkyl" refers to an alkyl substituent that is heteroatom-containing, the term "heterocyclic" refers to a cyclic substituent that is heteroatom-containing, the term "heteroaryl" refers to an aryl substituent that is heteroatom-containing, and the like. When the term "heteroatom-containing" appears prior to a list of possible heteroatom-containing groups, it is intended that the term apply to every member of that group. That is, the phrase "heteroatom-containing alkyl, alkenyl, and alkynyl" is to be interpreted as "heteroatom-containing alkyl, heteroatom-containing alkenyl, and heteroatom-containing alkynyl."

By "substituted" as in "substituted alkyl," "substituted alkenyl," "substituted aryl," and the like, as alluded to in some of the aforementioned definitions, is meant that in the alkyl, alkenyl, aryl, or other moiety, at least one hydrogen atom bound to a carbon atom is replaced with one or more substituents that are functional groups such as hydroxyl, alkoxy, thio, amino, halo, and the like.

The terms "alkyl," "alkenyl," "aryl," and the like are, unless otherwise indicated, intended to include unsubstituted, substituted, heteroatom-containing, and substituted heteroatom-containing such substituents.

II. Topical Formulations

Any cosmeceutically active base may be used at a concentration sufficient to provide a pH at the region of the a pH at the skin surface within the range of about 8.0–13.0, preferably about 8.0–11.5, more preferably about 8.5–11.5, and most preferably about 8.5–10.5, to produce a cream, lotion, solution, spray, gel, ointment, paste or the like, and/or may be prepared so as to contain liposomes, micelles, and/or microspheres, for use in a method of treating an aging-related skin condition.

A. Cosmeceutically Active Bases

In accordance with the invention described herein, the synthetic or naturally occurring suitable bases may be classified into two groups, namely (I) hydroxide-releasing agents and (II) nitrogenous organic bases.

Inorganic Bases

Exemplary inorganic bases are inorganic hydroxides, inorganic oxides, inorganic salts of weak acids, and combinations thereof. Preferred inorganic bases are those whose aqueous solutions have a high pH, and are acceptable as pharmaceutical or cosmeceutical additives, or as food additives. Examples of such preferred inorganic bases include those listed below. Some of the bases are identified in the form of a hydrate, and it is understood that when referring to a "base", both the hydrated and non-hydrated forms are intended to be included.

| Inorganic base | pH of Aqueous Solution (concentration) |
| --- | --- |
| Ammonium hydroxide[1,2,3] | 11.27 (1 N), 10.27 (0.001 N) |
| Sodium hydroxide[1,2,3] | 14 (5%), 13 (0.5%), 12 (0.05%) |
| Potassium hydroxide[1,2,3] | 13.5 (0.1 M) |

-continued

| Inorganic base | pH of Aqueous Solution (concentration) |
|---|---|
| Calcium hydroxide[1,3] | 12.4 (saturated solution in water) |
| Magnesium hydroxide[1,3] | 9.5 to 10.5 slurry |
| Magnesium oxide[1,2,3] | 10.3 (saturated aqueous solution) |
| Calcium oxide[3] | Soluble in water, Form Ca(OH)$_2$ |
| Sodium acetate[1,3] | ~8.9 (0.1 N) |
| Sodium acetate, trihydrate[1,2] | 8.9 (0.1 N) |
| Sodium acetate, anhydrous[1,2] | ~8.9 (0.1 N) |
| Sodium borate decahydrate[1,2] | ~8.8–9.4, 9.15 to 9.2 (0.01 M) |
| Sodium borate[1,2,3] | 8.8–9.4, 9.15 to 9.2 (0.01 M) |
| Sodium metaborate | Strongly alkaline |
| Sodium carbonate[1,2,3] | ~11.6 |
| Sodium carbonate hydrate[1] | ~11.6 |
| Sodium carbonate anhydrous | ~11.6 |
| Sodium bicarbonate[1,2,3] | 8.3 (0.1 M fresh) |
| Sodium phosphate, tribasic[1,3] | ~11.5 (0.1%), ~11.7 (0.5%), ~11.9 (1.0%) |
| Sodium phosphate, tribasic dodecahydrate | 11.5 (0.1%), 11.7 (0.5%), 11.9 (1.0%) |
| Sodium phosphate, dibasic, anhydrous[1,2] | 9.1 (1%) |
| Sodium phosphate, dibasic, heptahydrate[1,2] | ~9.5 |
| Sodium phosphate, dibasic[1,3] | ~9.5 |
| Sodium phosphate, dibasic, dihydrate[1] | ~9.5 |
| Sodium phosphate, dibasic, dodecahydrate | ~9.5 |
| Potassium carbonate[1,3] | ~11.6 |
| Potassium bicarbonate[3] | 8.2 (0.1 M) |
| Potassium citrate[1,2,3] | ~8.5 |
| Potassium citrate monohydrate | ~8.5 |
| Potassium acetate[1,3] | 9.7 (0.1 M) |
| Potassium phosphate, dibasic[1,2] | Aqueous solution is slightly alkaline |
| Potassium phosphate, tribasic[3] | Aqueous solution is strongly alkaline |
| Ammonium phosphate, dibasic[1,2,3] | ~8 |

[1] listed in the "Chemicals in Compliance with Pharmaceutical Standards: Inactive Ingredient Guide"
[2] listed in the "Handbook of Pharmaceutical Additives"
[3] listed in the FDA's food additive database Inorganic Hydroxides Inorganic hydroxides include, for example, ammonium hydroxide, alkali metal hydroxide and alkaline earth metal hydroxides, and mixtures thereof. Preferred inorganic hydroxides include ammonium hydroxide; monovalent alkali metal hydroxides such as sodium hydroxide and potassium hydroxide; divalent alkali earth metal hydroxides such as calcium hydroxide and magnesium hydroxide; and combinations thereof.

The amount of inorganic hydroxide included in the compositions and systems of the invention, will typically represent about 0.3–7.0 wt %, preferably 0.5–4.0 wt %, more preferably about 0.5–3.0 wt %, most preferably about 0.75–2.0 wt %, of a topically applied formulation.

For formulations and systems containing chemical compounds that can be neutralized by or react with the inorganic base (i.e., acidic inactive ingredients), the amount of inorganic hydroxide is preferably the total of (1) the amount necessary to neutralize any such compounds (i.e., the "acidic species"), plus (2) about 0.3–7.0 wt %, preferably 0.5–4.0 wt%, more preferably about 0.5–3.0 wt %, most preferably about 0.75–2.0 wt %, of the formulation or system. As an example, for an acid addition salt, the base is preferably present in an amount just sufficient to neutralize the salt, plus an additional amount (i.e., about 0.3–7.0 wt %, preferably 0.5–4.0 wt %, more preferably about 0.5–3.0 wt %, most preferably about 0.75–2.0 wt %). Basic compounds in the form of a neutral, free base or a basic salt of an acidic compound are usually not affected by a base, and thus, for these compounds, the amount in (1) is usually the amount necessary to neutralize inactive components that are acidic. For delivery systems (i.e., "patches" to be applied to the skin), the aforementioned percentages are given relative to the total weight of the formulation components and the adhesive, gel, or liquid reservoir.

Inorganic Oxides

Inorganic oxides include, for example, magnesium oxide, calcium oxide, and the like.

The amount of inorganic oxide included in the compositions and systems of the invention may be substantially higher than the numbers set forth above for the inorganic hydroxide, and may be as high as 20 wt %, in some cases as high as 25 wt % or higher, but will generally be in the range of about 2–20 wt %. These amounts may be adjusted to take into consideration the presence of any base-neutralizable species.

Inorganic Salts of Weak Acids

Inorganic salts of weak acids include, ammonium phosphate (dibasic); alkali metal salts of weak acids such as sodium acetate, sodium borate, sodium metaborate, sodium carbonate, sodium bicarbonate, sodium phosphate (tribasic), sodium phosphate (dibasic), potassium carbonate, potassium bicarbonate, potassium citrate, potassium acetate, potassium phosphate (dibasic), potassium phosphate (tribasic); alkaline earth metal salts of weak acids such as magnesium phosphate and calcium phosphate; and the like, and combinations thereof.

Preferred inorganic salts of weak acids include, ammonium phosphate (dibasic) and alkali metal salts of weak acids.

The amount of any inorganic salt of a weak acid included in the compositions and systems of the invention may be substantially higher than the numbers set forth above for the inorganic hydroxide, and may be as high as 20 wt %, in some cases as high as 25 wt % or higher, but will generally be in the range of approximately 2–20 wt %. These amounts may be adjusted to take into consideration the presence of any base-neutralizable species.

Organic Bases

Organic bases suitable for use in the invention are nitrogenous compounds having an amino group, amido group, an oxime, a cyano group, an aromatic or non-aromatic nitrogen-containing heterocycle, a urea group, and combinations thereof. More specifically, examples of suitable organic bases are nitrogenous bases, which include, but are not limited to, primary amines, secondary amines, tertiary amines, amides, oximes, nitriles, aromatic and non-aromatic nitrogen-containing heterocycles, urea, and mixtures thereof. For nitrogenous bases, the amount of enhancing agent will typically represent about 0.5–4.0 wt %, preferably about 0.5–3.0 wt %, more preferably about 0.75–2.0 wt %, of the topically applied formulation. These amounts may be adjusted to take into consideration the presence of any base-neutralizable species. Still greater amounts of the nitrogenous base may be used, if desired, depending on the strength of the particular base.

Preferred organic bases are those whose aqueous solutions have a high pH or a high pKa (more preferably a pKa>9), and are acceptable as food or pharmaceutical additives. Examples of such preferred organic bases are those listed below.

| Organic base | pH of Aqueous Solution (concentration) |
| --- | --- |
| 2-amino-2-methyl-1,3-propanediol[1] | 10.8 (0.1 m) |
| 2-amino-2-methyl-1-propanol[1] | 11.3 (0.1 m) |
| Diethanolamine[1] | 11.0 (0.1 N) |
| Triethanolamine[1] | 10.5 (0.1 N) |
| Butylamine[2] | pKa = 10.56 |
| Dimethylamine[2] | Strong base, pKa = 10.73 |
| Cyclohexylamine[2] | Strong base, pKa = 10.64 |
| Ethylenediamine[2] | Strong base, pKa = 10.71 |
| Isopentylamine[2] | pKa = 10.6 |
| Monoethanolamine[2] | 12.1 (25%), 12.05 (0.1 N), pKa = 9.4 |
| Phenethylamine[2] | Strong base, pKa = 9.83 |
| Piperidine[2] | Strong base, pKa = 11.12 |
| Pyrrolidine[2] | Strong base, pKa = 11.27 |
| Trimethylamine[2] | Strong base, pKa = 9.81 |

[1]listed in the "Handbook of Pharmaceutical Additives"
[2]listed in the FDA's food additive database Suitable nitrogenous bases may contain any one or a combination of the following:

primary amino (—$NH_2$) groups;

mono-substituted (secondary) amino groups —NHR where R is hydrocarbyl, generally either alkyl or aryl, e.g., lower alkyl or phenyl, and may be substituted with one or more nonhydrocarbyl substituents, e.g., 1 to 3 halo, hydroxyl, thiol, or lower alkoxy groups (such —NHR groups include, for example, methylamino, ethylamino, isopropylamino, butylamino, cyclopropylamino, cyclohexylamino, n-hexylamino, phenylamino, benzylamino, chloroethylamino, hydroxyethylamino, etc.);

di-substituted (tertiary) amino groups —$NR^aR^b$ where $R^a$ and $R^b$ may be the same or different and are as defined above for R (suitable —$NR^aR^b$ include, for example, dimethylamino, diethylamino, diisopropylamino, dibutylamino, methylpropylamino, methylhexylamino, methylcyclohexylamino, ethylcyclopropylamino, ethylchloroethylamino, methylbenzylamino, methylphenylamino, methyltoluylamino, methyl-p-chlorophenylamino, methylcyclohexylamino, etc.);

amides —(CO)—$NR^cR^d$ where $R^c$ and $R^d$ may be the same or different and are either hydrogen or R, wherein R is as defined above (including, for example, amides wherein one of $R^c$ and $R^d$ is H and the other is methyl, butyl, benzyl, etc.);

cyano (—CN);

aromatic nitrogen-containing heterocycles, typically five- or six-membered monocyclic substituents, or bicyclic fused or linked five- or six-membered rings (such as pyrrolyl, pyrrolidinyl, pyridinyl, quinolinyl, indolyl, pyrimidinyl, imidazolyl, 1,2,4-triazolyl, tetrazolyl, etc.); and non-aromatic nitrogen-containing heterocycles, typically four- to six-membered rings, including lactams and imides, e.g., pyrrolidino, morpholino, piperazino, piperidino, N-phenyl-propiolactam, -butyrolactam, -caprolactam, acetimide, phthalimide, succinimide, etc.

Primary amines, secondary amines, and tertiary amines may be generically grouped as encompassed by the molecular structure $NR^1R^2R^3$ wherein $R^1$, $R^2$, and $R^3$ are selected from H, alkyl, hydroxyalkyl, alkoxyalkyl, alkenyl, hydroxyalkenyl, alkoxyalkenyl, cycloalkyl, cycloalkyl-substituted alkyl, monocyclic aryl, and monocyclic aryl-substituted alkyl, any of which, with the exception of H, may be substituted with at least one nonhydrogen substituent (e.g., halide or an additional amine moiety —$NR^1R^2$), with the proviso that at least one of $R^1$, $R^2$, and $R^3$ is other than H. Examples of such amines include, without limitation, diethanolamine, triethanolamine, isopropanolamine, triisopropanolamine, dibutanol amine, tributanol amine, N-dodecylethanolamine, N—(2-methoxyethyl)dodecylamine, N—(2,2-dimethoxyethyl)dodecylamine, N-ethyl-N—(dodecyl) ethanolamine, N-ethyl-N—(2-methoxyethyl)dodecylamine, N-ethyl-N—(2,2-dimethoxyethyl) dodecylamine, dimethyldodecylamine-N-oxide, monolauroyl lysine, dipalmitoyl lysine, dodecylamine, stearylamine, phenylethylamine, triethylamine, PEG-2 oleamine, PEG-5 oleamine, dodecyl 2-(N,N-dimethylamino)propionate, bis(2-hydroxyethyl) oleyl-amine, and combinations thereof.

Exemplary primary amines include 2-aminoethanol, 2-aminoheptane, 2-amino-2-methyl-1,3 propanediol, 2-amino-2-methyl-1-propanol, n-amylamine, benzylamine, 1,4-butanediamine, n-butylamine, cyclohexylamine, ethylamine, ethylenediamine, methylamine, α-methylbenzylamine, phenethylamine, propylamine, and tris(hydroxymethyl)aminomethane.

Exemplary secondary amines include compounds that contain groups such as methylamino, ethylamino, isopropylamino, butylamino, cyclopropylamino, cyclohexylamino, n-hexylamino, phenylamino, benzylamino, chloroethylamino, hydroxyethylamino, and so forth. Exemplary secondary amines include diethanolamine, diethylamine, diisopropylamine, and dimethylamine.

Exemplary tertiary amines include compounds that contain groups such as dibutylamino, diethylamino, dimethylamino, diisopropylamino, ethylchloroethylamino, ethylcyclopropylamino, methylhexylamino, methylcyclohexylamino, methylpropylamino, methylbenzylamino, methyl-p-chlorophenylamino, methylcyclohexylamino, methylphenylamino, methyltoluylamino, and so forth. Exemplary tertiary amines include N,N-diethylaniline, N,N-dimethylglycine, triethanolamine, triethylamine, and trimethylamine.

Amides, as will be appreciated by those in the art, have the molecular structure $R^4$—(CO)—$NR^5R^6$ where $R^4$, $R^5$, and $R^6$ are generally selected from H, alkyl, cycloalkyl, cycloalkyl-substituted alkyl, monocyclic aryl, and monocyclic aryl-substituted alkyl, any of which, with the exception of H, may be substituted with at least one nonhydrogen substituent as indicated with respect to amine compounds of formula $NR^1R^2R^3$. Examples of suitable amides herein include, without limitation, hexamethyleneacetamide, hexamethyleneoctamide, hexamethylene lauramide, hexamethylene palmitamide, N,N-dimethyl formamide, N,N-dimethyl acetamide, N,N-dimethyloctamide, N,N-dimethyldecamide, toluamide, dimethyl-m-toluamide, diethyl-m-toluamide, and combinations thereof.

Nitrogen-containing heterocycles suitable as the cosmeceutically active base herein include, by way of example, 2-pyrrolidone, 1-methyl-2-pyrrolidone, 5-methyl-2-pyrrolidone, 1,5-dimethyl-2-pyrrolidone, 1-ethyl-2-pyrrolidone, 1-propyl-3-dodecylpyrrolidine, 1-dodecyclazacycloheptan-2-one, ethylene thiourea, hydantoin, oxalylurea, imidazolidilyl urea, N-octadecyl morpholine, dodecylpyridinium, N-dodecylpyrrolidine, N-dodecylpiperidine, N-dodecylhomopiperidine, and combinations thereof.

For all cosmeceutically active bases herein, including both organic and inorganic bases, the optimum amount of any particular base will depend on the strength or weakness of the base, the molecular weight of the base, and other factors. One skilled in the art may readily determine the optimum amount of any particular base by ensuring that a formulation is effective to provide a pH at the skin surface, following application of the formulation, in the range of about 8.0–13.0, preferably about 8.0–11.5, more preferably about 8.5–11.5, and most preferably about 8.5–10.5. This in turn ensures that the degree of treatment is maximized while the possibility of damage to the skin is eliminated or at least substantially minimized.

B. Formulation Types

The pharmaceutical formulation of the invention comprises a pharmaceutically acceptable topical carrier and an active agent that consists essentially of a cosmeceutically active base.

The particular combination of components in the formulation is determined in large part by chemical compatibility. That is, each component must coexist in the topical pharmaceutical formulation together with the base without reacting or otherwise interacting with each other in a way that would diminish therapeutic efficacy or increase the likelihood of toxic or other adverse effects. Thus, for example, direct contact between a strong inorganic base, such as potassium hydroxide, and an acid, such as kojic acid, should be avoided, as such compounds may react with each other in deleterious ways. Even such reactive pairs of compounds may, however, be combined in an effective topical formulation if, for example, the active agent is contained within liposomes, micelles, microspheres, or similar structures, so that it is released after permeation into the skin and after the base has dissipated sufficiently to avoid significant reaction with the active agent.

The formulation may be in any form suitable for application to the body surface, such as a cream, lotion, solution, gel, ointment, paste, plaster, paint, bioadhesive, or the like, and/or may be prepared so as to contain liposomes, micelles, and/or microspheres. For those formulations in which the base is an inorganic base, such as a hydroxide-releasing agent, it is preferred although not essential that water be present. Thus, such a formulation may be aqueous, i.e., contain water, or may be nonaqueous and optionally used in combination with an occlusive overlayer so that moisture evaporating from the body surface is maintained within the formulation upon application to the body surface and thereafter.

Formulations of the invention may optionally contain a pharmaceutically acceptable viscosity enhancer and/or film former. A viscosity enhancer increases the viscosity of the formulation so as to inhibit its spread beyond the site of application. Balsam Fir (Oregon) is an example of a pharmaceutically acceptable viscosity enhancer.

A film former, when it dries, forms a protective film over the site of application. The film inhibits removal of the active ingredient and keeps it in contact with the site being treated. An example of a film former that is suitable for use in this invention is Flexible Collodion, USP. As described in *Remington: The Science and Practice of Pharmacy*, 19th Ed. (Easton, Pa.: Mack Publishing Co., 1995), at page 1530, collodions are ethyl ether/ethanol solutions containing pyroxylin (a nitrocellulose) that evaporate to leave a film of pyroxylin. A film former may act additionally as a carrier. Solutions that dry to form a film are sometimes referred to as paints.

As noted above, the present topical formulations may take any of a wide variety of forms, and include, for example, creams, lotions, solutions, sprays, gels, ointments, pastes or the like, and/or may be prepared so as to contain liposomes, micelles, and/or microspheres.

Creams, as is well known in the arts of pharmaceutical and cosmeceutical formulation, are viscous liquids or semisolid emulsions, either oil-in-water or water-in-oil. Cream bases are water-washable, and contain an oil phase, an emulsifier, and an aqueous phase. The oil phase, also called the "internal" phase, is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation is generally a nonionic, anionic, cationic or amphoteric surfactant.

Lotions, which are preferred for delivery of cosmetic agents, are preparations to be applied to the skin surface without friction, and are typically liquid or semiliquid preparations in which solid particles, including the active agent, are present in a water or alcohol base. Lotions are usually suspensions of solids, and preferably, for the present purpose, comprise a liquid oily emulsion of the oil-in-water type. Lotions are preferred formulations herein for treating large body areas, because of the ease of applying a more fluid composition. It is generally necessary that the insoluble matter in a lotion be finely divided. Lotions will typically contain suspending agents to produce better dispersions as well as compounds useful for localizing and holding the active agent in contact with the skin, e.g., methylcellulose, sodium carboxymethyl-cellulose, or the like.

Solutions are homogeneous mixtures prepared by dissolving one or more chemical substances (solutes) in a liquid such that the molecules of the dissolved substance are dispersed among those of the solvent. The solution may contain other cosmeceutically acceptable chemicals to buffer, stabilize or preserve the solute. Common examples of solvents used in preparing solutions are ethanol, water, propylene glycol or any other cosmeceutically acceptable vehicles.

As is of course well known, gels are semisolid, suspension-type systems. Single-phase gels contain organic macromolecules distributed substantially uniformly throughout the carrier liquid, which is typically aqueous, but also, preferably, contain an alcohol, and, optionally, an oil. Preferred "organic macromolecules," i.e., gelling agents, are crosslinked acrylic acid polymers such as the "carbomer" family of polymers, e.g., carboxypolyalkylenes that may be obtained commercially under the Carbopol® trademark. Also preferred are hydrophilic polymers such as polyethylene oxides, polyoxyethylene-polyoxypropylene copolymers and polyvinylalcohol; cellulosic polymers such as hydroxypropyl cellulose, hydroxyethyl cellulose, hydroxypropyl methylcellulose, hydroxypropyl methylcellulose phthalate, and methyl cellulose; gums such as tragacanth and xanthan gum; sodium alginate; and gelatin. In order to prepare a uniform gel, dispersing agents such as alcohol or glycerin can be added, or the gelling agent can be dispersed by trituration, mechanical mixing or stirring, or combinations thereof.

Ointments, as also well known in the art, are semisolid preparations that are typically based on petrolatum or other petroleum derivatives. The specific ointment base to be used, as will be appreciated by those skilled in the art, is one that will provide for a number of desirable characteristics, e.g., emolliency or the like. As with other carriers or vehicles, an ointment base should be inert, stable, nonirritating, and nonsensitizing. As explained in *Remington: The Science and Practice of Pharmacy*, 19th Ed. (Easton, Pa.: Mack Publishing Co., 1995), at pages 1399–1404, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin, and hydrophilic petrolatum. Emulsion ointment bases are either water-in-oil (W/O) emulsions or oil-in-water (O/W) emulsions, and include, for example, cetyl alcohol, glyceryl monostearate, lanolin, and stearic acid. Preferred water-soluble ointment bases are prepared from polyethylene glycols of varying molecular weight; again, see *Remington: The Science and Practice of Pharmacy* for further information.

Pastes are semisolid dosage forms in which the active agent is suspended in a suitable base. Depending on the nature of the base, pastes are divided between fatty pastes or those made from single-phase aqueous gels. The base in a fatty paste is generally petrolatum or hydrophilic petrolatum or the like. The pastes made from single-phase aqueous gels generally incorporate carboxymethylcellulose or the like as a base.

Formulations may also be prepared with liposomes, micelles, and microspheres. Liposomes are microscopic vesicles having a lipid wall comprising a lipid bilayer, and, in the present context, encapsulate one or more components of the anti-aging formulations. Liposomal preparations herein include cationic (positively charged), anionic (negatively charged), and neutral preparations. Cationic liposomes are readily available. For example, N[1-2,3-dioleyloxy)propyl]-N,N,N-triethylammonium (DOTMA) liposomes are available under the tradename Lipofectin® (GIBCO BRL, Grand Island, N.Y.). Similarly, anionic and neutral liposomes are readily available as well, e.g., from Avanti Polar Lipids (Birmingham, Ala.), or can be easily prepared using readily available materials. Such materials include phosphatidyl choline, cholesterol, phosphatidyl ethanolamine, dioleoylphosphatidyl choline (DOPC), dioleoylphosphatidyl glycerol (DOPG), and dioleoylphoshatidyl ethanolamine (DOPE), among others. These materials can also be mixed with DOTMA in appropriate ratios. Methods for making liposomes using these materials are well known in the art.

Micelles are known in the art as comprised of surfactant molecules arranged so that their polar headgroups form an outer spherical shell, while the hydrophobic, hydrocarbon chains are oriented towards the center of the sphere, forming a core. Micelles form in an aqueous solution containing surfactant at a high enough concentration so that micelles naturally result. Surfactants useful for forming micelles include, but are not limited to, potassium laurate, sodium octane sulfonate, sodium decane sulfonate, sodium dodecane sulfonate, sodium lauryl sulfate, docusate sodium, decyltrimethylammonium bromide, dodecyltrimethylammonium bromide, tetradecyltrimethylammonium bromide, tetradecyltrimethyl-ammonium chloride, dodecylammonium chloride, polyoxyl-8 dodecyl ether, polyoxyl-12 dodecyl ether, nonoxynol 10, and nonoxynol 30.

Microspheres, similarly, may be incorporated into the present formulations. Like liposomes and micelles, microspheres essentially encapsulate one or more components of the present formulations. They are generally although not necessarily formed from lipids, preferably charged lipids such as phospholipids. Preparation of lipidic microspheres is well known in the art and described in the pertinent texts and literature.

C. Additives

Various additives, known to those skilled in the art, may be included in the topical formulations. For example, solvents, including relatively small amounts of alcohol, may be used to solubilize certain formulation components. Although the cosmeceutically active bases herein do penetrate into the skin and have in fact been described as skin permeation enhancers, it may be desirable, with weaker bases or particularly severe skin conditions, to include an added permeation enhancer in the formulation. Examples of suitable enhancers include, but are not limited to, ethers such as diethylene glycol monoethyl ether (available commercially as Transcutol®) and diethylene glycol monomethyl ether; surfactants such as sodium laurate, sodium lauryl sulfate, cetyltrimethylammonium bromide, benzalkonium chloride, Poloxamer® (231, 182, 184), Tween® (20, 40, 60, 80), and lecithin (U.S. Pat. No. 4,783,450); alcohols such as ethanol, propanol, octanol, benzyl alcohol, and the like; polyethylene glycol and esters thereof such as polyethylene glycol monolaurate (PEGML; see, e.g., U.S. Pat. No. 4,568,343); amides and other nitrogenous compounds such as urea, dimethylacetamide (DMA), dimethylformamide (DMF), 2-pyrrolidone, 1-methyl-2-pyrrolidone, ethanolamine, diethanolamine, and triethanolamine; terpenes; alkanones; and organic acids, particularly citric acid and succinic acid. Azone® and sulfoxides such as DMSO and $C_{10}MSO$ may also be used, but are less preferred.

Most preferred enhancers are those lipophilic co-enhancers typically referred to as "plasticizing" enhancers, i.e., enhancers that have a molecular weight in the range of about 150 to 1000, an aqueous solubility of less than about 1 wt. %, preferably less than about 0.5 wt. %, and most preferably less than about 0.2 wt. %. The Hildebrand solubility parameter of plasticizing enhancers is in the range of about 2.5 to about 10, preferably in the range of about 5 to about 10. Preferred lipophilic enhancers are fatty esters, fatty alcohols, and fatty ethers. Examples of specific and most preferred fatty acid esters include methyl laurate, ethyl oleate, propylene glycol monolaurate, propylene glycol dilaurate, glycerol monolaurate, glycerol monooleate, isopropyl n-decanoate, and octyldodecyl myristate. Fatty alcohols include, for example, stearyl alcohol and oleyl alcohol, while fatty ethers include compounds wherein a diol or triol, preferably a $C_2$–$C_4$ alkane diol or triol, are substituted with one or two fatty ether substituents.

Additional permeation enhancers will be known to those of ordinary skill in the art of topical drug delivery, and/or are described in the pertinent texts and literature. See, e.g., *Percutaneous Penetration Enhancers,* eds. Smith et al. (CRC Press, 1995).

Various other additives may be included in the compositions of the present invention in addition to those identified above. These include, but are not limited to, antioxidants, astringents, perfumes, preservatives, emollients, pigments, dyes, humectants, propellants, and sunscreen agents, as well as other classes of materials whose presence may be cosmetically, medicinally or otherwise desirable. Typical examples of optional additives for inclusion in the formulations of the invention are as follows: preservatives such as sorbate; solvents such as isopropanol and propylene glycol; astringents such as menthol and ethanol; emollients such as polyalkylene methyl glucosides; humectants such as glycerine; emulsifiers such as glycerol stearate, PEG-100 stearate, polyglyceryl-3 hydroxylauryl ether, and polysorbate 60; sorbitol and other polyhydroxyalcohols such as polyethylene glycol; sunscreen agents such as octyl methoxyl cinnamate (available commercially as Parsol MCX) and butyl methoxy benzoylmethane (available under the tradename Parsol 1789); antioxidants such as ascorbic acid (vitamin C), α-tocopherol (Vitamin E), β-tocopherol, γ-tocopherol, δ-tocopherol, ε-tocopherol, $\zeta_1$-tocopherol, $\zeta_2$-tocopherol, η-tocopherol, and retinol (vitamin A); essential oils, ceramides, essential fatty acids, mineral oils, vegetable oils (e.g., soya bean oil, palm oil, liquid fraction of shea butter, sunflower oil), animal oils (e.g., perhydrosqualene), synthetic oils, silicone oils or waxes (e.g., cyclomethicone and dimethicone), fluorinated oils (generally perfluoropolyethers), fatty alcohols (e.g., cetyl alcohol), and waxes (e.g., beeswax, carnauba wax, and paraffin wax); skin-feel modifiers; and thickeners and structurants such as swelling clays and cross-linked carboxypolyalkylenes that may be obtained commercially under the Carbopol® trademark.

Other additives include beneficial agents such as those materials that condition the skin (particularly, the upper layers of the skin in the stratum corneum) and keep it soft by retarding the decrease of its water content and/or protect the skin. Such conditioners and moisturizing agents include, by way of example, pyrrolidine carboxylic acid and amino acids; organic antimicrobial agents such as 2,4,4'-trichloro-2-hydroxy diphenyl ether (triclosan) and benzoic acid; anti-inflammatory agents such as acetylsalicylic acid and glycyrrhetinic acid; anti-seborrhoeic agents such as retinoic acid; vasodilators such as nicotinic acid; inhibitors of melanogenesis such as kojic acid; and mixtures thereof. Other advantageous include cosmeceutically active agents in addition to the cosmeceutically active base. Such additional cosmeceutically active agents include, for example, alpha hydroxyacids, alpha ketoacids, polymeric hydroxyacids, moisturizers, collagen, marine extract, and antioxidants such as ascorbic acid (vitamin C), α-tocopherol (Vitamin E), β-tocopherol, γ-tocopherol, δ-tocopherol, ε-tocopherol, $\zeta_1$-tocopherol, $\zeta_2$-tocopherol, η-tocopherol, and retinol (vitamin A), and/or cosmetically acceptable salts, esters, amides, or other derivatives thereof. A preferred tocopherol compound is α-tocopherol. Additional cosmetic agents include those that are capable of improving oxygen supply in skin tissue, as described, for example, in Gross, et al, WO 94/00098 and Gross, et al, WO 94/00109, both assigned to Lancaster Group AG. Sunscreens may also be included.

Other embodiments may include a variety of non-carcinogenic, non-irritating healing materials that facilitate treatment with the formulations of the invention. Such healing materials may include nutrients, minerals, vitamins, electrolytes, enzymes, herbs, plant extracts, glandular or animal extracts, or safe therapeutic agents that may be added to the formulation to facilitate the healing of dermal disorders.

The amounts of these various additives are those conventionally used in the cosmetics field, and range, for example, from about 0.01% to about 20% of the total weight of the topical formulation.

The formulations of the invention may also include conventional additives such as opacifiers, fragrance, colorant, gelling agents, thickening agents, stabilizers, surfactants, and the like. Other agents may also be added, such as antimicrobial agents, to prevent spoilage upon storage, i.e., to inhibit growth of microbes such as yeasts and molds. Suitable antimicrobial agents are typically selected from the group consisting of the methyl and propyl esters of p-hydroxybenzoic acid (i.e., methyl and propyl paraben), sodium benzoate, sorbic acid, imidurea, and combinations thereof.

The formulations may also contain irritation-mitigating additives to minimize or eliminate the possibility of skin irritation or skin damage resulting from the chemical entity to be administered, or other components of the composition. Suitable irritation-mitigating additives include, for example: α-tocopherol; monoamine oxidase inhibitors, particularly phenyl alcohols such as 2-phenyl-1-ethanol; glycerin; salicylates; ascorbates; ionophores such as monensin; amphiphilic amines; animonium chloride; N-acetylcysteine; capsaicin; and chioroquine. The irritation-mitigating additive, if present, may be incorporated into the compositions at a concentration effective to mitigate irritation or skin damage, typically representing not more than about 20 wt. %, more typically not more than about 5 wt. %, of the formulation.

The formulations of the invention may also contain a therapeutically effective amount of a pharmacologically active agent suitable for topical administration. Such agents include an asymmetrical lamellar aggregate consisting of phospholipids and oxygen-loaded fluorocarbon or a fluorocarbon compound mixture, which are capable of improving oxygen supply in skin tissue, as described, for example, in International Patent Publication Nos. WO 94/00098 and WO 94/00109.

Suitable pharmacologically active agents that may be incorporated into the present formulations and thus topically applied along with the cosmeceutically active base include, but are not limited to, the following: agents that improve or eradicate pigmented or non-pigmented age spots, keratoses, and wrinkles; antimicrobial agents; antibacterial agents; antipruritic and antixerotic agents; antiinflammatory agents; local anesthetics and analgesics; corticosteroids; retinoids; vitamins; hormones; and antimetabolites.

Some examples of topical pharmacologically active agents include acyclovir, amphotericins, chlorhexidine, clotrimazole, ketoconazole, econazole, miconazole, metronidazole, minocycline, nystatin, neomycin, kanamycin, phenytoin, para-amino benzoic acid esters, octyl methoxycinnamate, octyl salicylate, oxybenzone, dioxybenzone, tocopherol, tocopheryl acetate, selenium sulfide, zinc pyrithione, diphenhydramine, pramoxine, lidocaine, procaine, erythromycin, tetracycline, clindamycin, crotamiton, hydroquinone and its monomethyl and benzyl ethers, naproxen, ibuprofen, cromolyn, retinol, retinyl palmitate, retinyl acetate, coal tar, griseofulvin, estradiol, hydrocortisone, hydrocortisone 21-acetate, hydrocortisone 17-valerate, hydrocortisone 17-butyrate, progesterone, betamethasone valerate, betamethasone dipropionate, triamcinolone acetonide, fluocinonide, clobetasol propionate, minoxidil, dipyridamole, diphenylhydantoin, benzoyl peroxide, and 5-fluorouracil, A pharmacological acceptable carrier may also be incorporated in the cosmeceutical formulation of the present invention and may be any carrier conventionally used in the art. Examples thereof include water, lower alcohols, higher alcohols, polyhydric alcohols, monosaccharides, disaccharides, polysaccharides, hydrocarbon oils, fats and oils, waxes, fatty acids, silicone oils, nonionic surfactants, ionic surfactants, silicone surfactants, and water-based mixtures and emulsion-based mixtures of such carriers.

III. Administration

The method of delivery of the active agent may vary, but necessarily involves application of a formulation of the invention to an area of skin prone to or affected by an aging-related skin condition, e.g., any skin condition or disorder associated with, caused by, or affected by, intrinsic aging and/or extrinsic aging. The aging-related skin condition may, for example, involve wrinkles, age spots, sun damage (particularly UV radiation-induced oxidative stress), blemishes, hyperpigmented skin, age spots, increased skin thickness, loss of skin elasticity and collagen content, dry skin, lentigines, and melasmas.

A cream, lotion, gel, ointment, paste or the like may be spread on the affected surface and gently rubbed in. A solution may be applied in the same way, but more typically will be applied with a dropper, swab, or the like, and carefully applied to the affected areas.

The application regimen will depend on a number of factors that may readily be determined, such as the severity of the condition and its responsiveness to initial treatment, but will normally involve one or more applications per day on an ongoing basis. One of ordinary skill may readily determine the optimum amount of the formulation to be administered, administration methodologies and repetition rates. In general, it is contemplated that the formulations of the invention will be applied in the range of once or twice weekly up to once or twice daily.

It is to be understood that while the invention has been described in conjunction with the preferred specific embodiments thereof, the foregoing description is intended to illustrate and not limit the scope of the invention. Other aspects, advantages, and modifications will be apparent to those skilled in the art to which the invention pertains. Furthermore, the practice of the present invention will employ, unless otherwise indicated, conventional techniques of cosmeceutical formulation that are within the skill of the art. Such techniques are fully explained in the literature. All patents, patent applications, and publications mentioned herein are hereby incorporated by reference in their entireties.

EXAMPLE 1

An in vitro keratolysis study was performed to compare the capability of glycolic acid and a base for removing protein from stratum corneum. Adult foot callus was collected, grounded and the portion between 50–80 mesh was used. Glycolic acid and sodium hydroxide solutions (concentration =0.05 M) were prepared in distilled water. Ten mg of ground callus powder was place in a test tube. Four ml of a test chemical was added to the callus and the test tube was placed in a shaker and incubated in a water bath at 37° C. for a predetermined incubation time. The incubation time periods were 10 min., 40 min, 2 hours, 4 hours, 6 hours and 24 hours. Six samples of each base were tested a total of six times each at each of the aforementioned incubation time periods.

At the end of each incubation period, the test tube was removed from the shaker and the test tube was centrifuged. The solution was removed and filtered, and the protein in the solution was then determined using a BioRad® protein assay kit. The results are shown in the following Table 1 and FIG. 1.

TABLE 1

Quantity of Protein Released Using Different Bases and Incubation Time Periods

| | Amount of Protein Released (mg/4 ml) | | | | | |
|---|---|---|---|---|---|---|
| | 10 min | 0 min | 2 hours | 4 hours | 6 hours | 24 hours |
| NaOH | 0.419 | 0.739 | 0.899 | 1.003 | 4.853 | 5.148 |
| Glycolic Acid | 0.093 | 0.175 | 0.126 | 0.219 | 0.089 | 0.173 |
| Water | 0.002 | 0.043 | 0.074 | 0.086 | 0.073 | 0.021 |

The results indicated that at all time points 0.05 M NaOH solutions released more protein when compared to glycolic acid solutions at the same concentration and water control. However, glycolic acid did not show statistical differences in comparison with water. Sodium hydroxide solutions the amounts of protein released at 6 hours and 24 hours were significantly higher than the amounts released at 10 minutes, 40 minutes, 2 hours and 4 hours.

EXAMPLE 2

Figure 2:
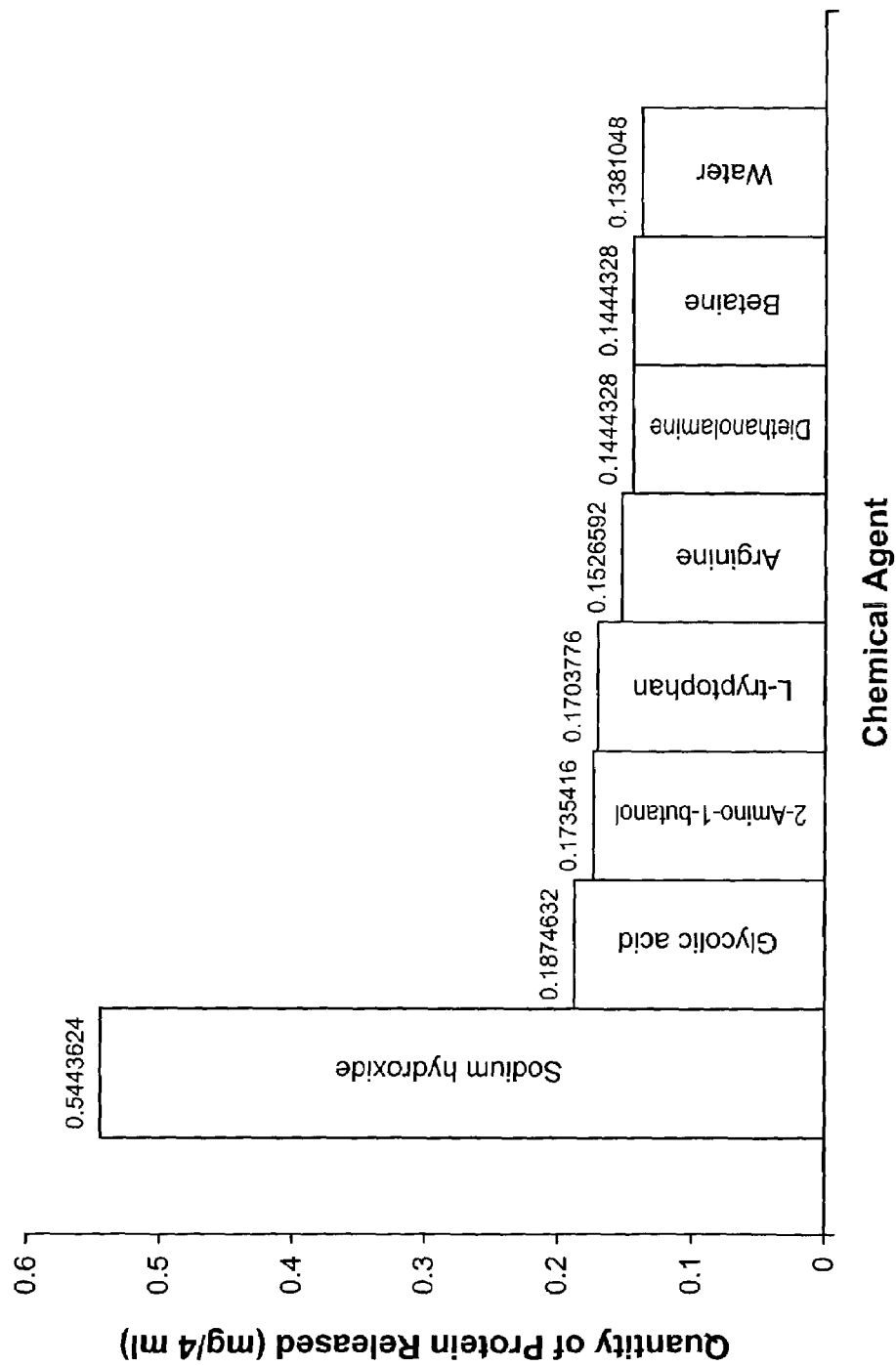
FIG. 2 is a graph illustrating the in vitro release of protein from the stratum corneum upon incubation for 10 minutes in glycolic acid and in 0.05 M solutions of different bases, as described in Example 2.

The procedure of Example 1 was then repeated to compare the capability of glycolic acid with respect to a number of different bases, including both inorganic and organic bases, with respect to removal of protein from stratum corneum. The results are shown in Table 2 (for the ten-minute incubation period) and FIG. 2.

TABLE 2

Quantity of Protein Released Using Different Bases (Incubation Time = 10 minutes)

| | Amount of Protein Released (mg/4 ml) |
|---|---|
| NaOH | 0.544 |
| Glycolic Acid | 0.187 |
| Diethanolamine | 0.144 |
| L-tryptophan | 0.170 |
| Arginine | 0.153 |
| 2-amino-1-butanol | 0.174 |
| Betaine | 0.144 |
| Water | 0.138 |

The results indicated that 0.05 M NaOH solutions released more protein when compared to glycolic acid, other bases tested at the same concentration and water control. However, glycolic acid did and other bases did not show significant differences in comparison with water.

EXAMPLE 3

Figure 3:
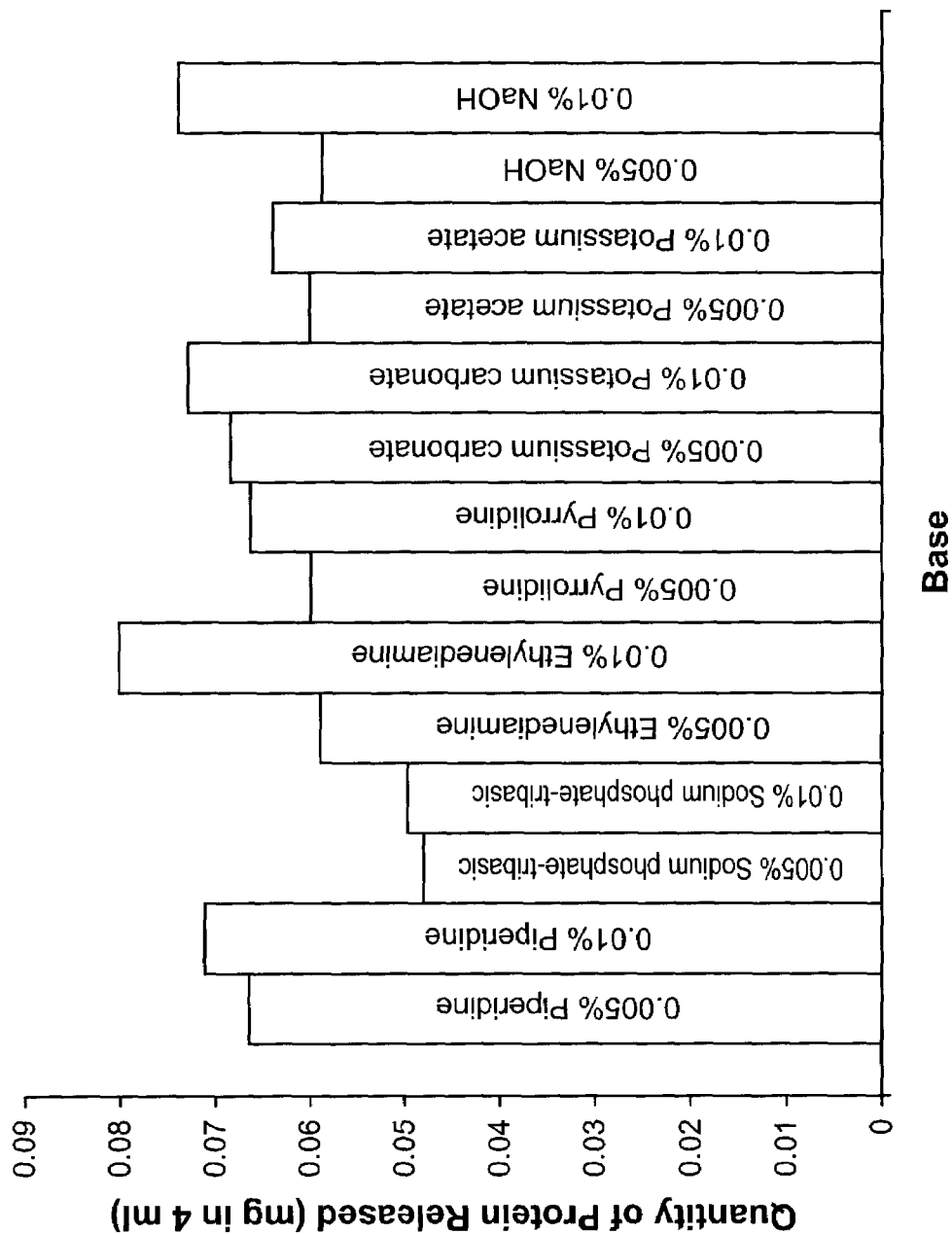
FIG. 3 is a graph illustrating the in vitro release of protein from the stratum corneum upon incubation in solutions of different bases (0.005 wt. % and 0.010 wt. %), at an incubation time of 40 minutes, as described in Example 3.

The procedure of Example 1 was then repeated with additional bases, all of which are listed in Table 3 (concentration=0.005% and 0.01%), using an incubation time period of 40 minutes. The results are shown in the following Table 3 and FIG. 3.

TABLE 3

Quantity of Protein Released Using Different Bases
(Incubating Time = 40 minutes)

| | Amount of Protein Released (mg/4 ml) | |
|---|---|---|
| | 0.005% | 0.01% |
| Piperidine | 0.066 | 0.071 |
| Sodium phosphate-tribasic | 0.048 | 0.050 |
| Ethylenediamine | 0.059 | 0.080 |
| Pyrrolidine | 0.060 | 0.066 |
| Potassium Carbonate | 0.068 | 0.073 |
| Potassium Acetate | 0.060 | 0.064 |
| NaOH | 0.059 | 0.074 |

The results indicate that solutions of bases listed in Table 3 released about the same amounts of protein at 0.005% and 0.01% concentrations. The quantity of protein released was very small when compared to the data obtained in Examples 1 and 2 at a higher concentration of base.

EXAMPLE 4

A cream composition containing 30% dodecylamine is formulated as follows. Dodecylamine (30 grams) is dissolved in propylene glycol (15 ml). The solution thus prepared is mixed with hydrophilic ointment (55 grams) until a consistent cream is obtained.

EXAMPLE 5

A cream composition containing 25% N,N-dimethyloctamide is formulated as follows. N,N-Dimethyloctamide (25 grams) is dissolved in propylene glycol (15 ml). The solution thus prepared is mixed with hydrophilic ointment (55 grams) until a consistent cream is obtained.

EXAMPLE 6

A solution composition containing 5% stearylamine, in oil-in-water emulsion is prepared as follows. Stearylamine, (5 grams) is dissolved in propylene glycol (10 ml). The solution is then mixed with hydrophilic ointment, USP grade (85 grams) and the mixing continued until a uniform consistency is obtained.

EXAMPLE 7

A cream composition containing 10% isopropanolamine in oil-in-water emulsion is prepared as follows. Isopropanolamine (10 grams) are dissolved in propylene glycol (20 ml). The solution is then mixed with hydrophilic ointment, USP grade (70 grams) and the mixing continued until a uniform consistency is obtained.

EXAMPLE 8

A cream composition containing 25% 1-ethyl-2-pyrrolidone, is formulated as follows. 1-Ethyl-2-pyrrolidone (25 grams) is dissolved in propylene glycol (5 ml). The solution thus prepared is mixed with hydrophilic ointment (70 grams) until a consistent cream is obtained.

EXAMPLE 9

A therapeutic composition containing 5% hydroquinone and 8% N-ethyl-N-(dodecyl)ethanolamine in solution form for age spots, melasmas, lentigines and other pigmented skin spots may be formulated as follows. N-Ethyl-N-(dodecyl)ethanol-amine (8 grams), hydroquinone (5 grams) and sodium metabisulfite (0.5 grams) are dissolved in a mixture of ethanol (70 ml), water (15 ml) and propylene glycol (7 ml) with stirring until a clear solution is obtained.

EXAMPLE 10

A therapeutic composition containing 5% hydrocortisone and 10% N-ethyl-N-(dodecyl)ethanolamine in solution form for use as an anti-inflammatory agent may be formulated as follows. N-Ethyl-N-(dodecyl)ethanolamine (10 grams), hydrocortisone (0.5 grams) are dissolved in a mixture of ethanol (70 ml), water (10 ml) and propylene glycol (10 ml) with stirring until a clear solution is obtained.

EXAMPLE 11

A therapeutic composition containing 5% hydroquinone and 8% N,N-dimethyldecamide in solution form for age spots, keratoses, melasmas, lentigines and other pigmented skin spots may be formulated as follows. N,N-Dimethyldecamide (8 grams), hydroquinone (5 grams) and sodium metabisulfite (0.5 grams) are dissolved in a mixture of ethanol (75 ml), water (10 ml) and propylene glycol (7 ml) with stirring until a clear solution is obtained.

EXAMPLE 12

A therapeutic composition containing 1% hydrocortisone and 8% N,N-dimethyloctamide in solution form for use as an anti-inflammatory agent may be formulated as follows. N,N-Dimethyloctamide (8 grams) and hydrocortisone (1 gram) are dissolved in a mixture of ethanol (70 ml), water (15 ml) and propylene glycol (7 ml) with stirring until a clear solution is obtained.

EXAMPLE 13

A therapeutic composition containing 2% kojic acid and 10% N-ethyl-N-(dodecyl)ethanolamine in solution form for age spots, keratoses, melasmas, lentigines and other pigmented skin spots may be formulated as follows. N-Ethyl-N-(dodecyl)ethanolamine (10 grams), kojic acid (2 grams) are dissolved in a mixture of ethanol (70 ml), water (10 ml) and propylene glycol (10 ml) with stirring until a clear solution is obtained.

EXAMPLE 14

A sunscreen composition containing 5% octyl dimethyl para-amino benzoate, 3% dioxybenzone and 2% hexamethyleneoctamide may be formulated as follows. Octyl dimethyl para-aminobenzoate (5 grams), dioxybenzone (3 grams) and hexamethyleneoctamide (2 grams) are dissolved in a mixture of ethanol (75 ml), water (10 ml) and propylene glycol (15 ml) with stirring until a clear solution is obtained.

EXAMPLE 15

A therapeutic composition containing 5% monolauroyl lysine to alleviate dry or flay skin may be formulated as follows. Monolauroyl lysine (5 grams) is dissolved in ethanol (20ml), and the solution thus obtained is mixed with hydrophilic ointment USP (75 grams) with stirring until a uniform consistency is obtained.

EXAMPLE 16

A therapeutic composition containing 0.5% hydrocortisone and 2% potassium phosphate (dibasic) in solution form for use as an anti-inflammatory agent may be formulated as follows. Potassium phosphate (dibasic) (2 grams) and hydrocortisone (0.5 grams) are dissolved in a mixture of ethanol (80 ml), water (15 ml) and propylene glycol (5 ml) with stirring until a clear solution is obtained.

EXAMPLE 17

A therapeutic composition containing 0.5% hydrocortisone and 2% sodium phosphate (tribasic) in solution form for use as an anti-inflammatory agent may be formulated as follows. Sodium phosphate (dibasic) (2 grams) and hydrocortisone (0.5 grams) are dissolved in a mixture of ethanol (80 ml), water (15 ml) and propylene glycol (5 ml) with stirring until a clear solution is obtained.

EXAMPLE 18

A therapeutic composition containing 3% hydroquinone and 5% potassium citrate in solution form for age spots, keratoses, melasmas, lentigines and other pigmented skin spots may be formulated as follows. Potassium citrate (5 grams), hydroquinone (3 grams) are dissolved in a mixture of ethanol (80 ml), water (10 ml) and propylene glycol (10 ml) with stirring until a clear solution is obtained.

EXAMPLE 19

A therapeutic composition containing 5% hydroquinone and 8% ammonium phosphate (dibasic) in solution form may be formulated as follows. Ammonium phosphate (dibasic) (8 grams), hydroquinone (5 grams) are dissolved in a mixture of ethanol (80 ml), water (10 ml) and propylene glycol (10 ml) with stirring until a clear solution is obtained.

EXAMPLE 20

A cream composition containing 10% isopropanolamine and 1% hydrocortisone in oil-in-water emulsion is prepared as follows. Isopropanolamine (10 grams) and hydrocortisone (1 gram) are dissolved in propylene glycol (20 ml). The solution is then mixed with hydrophilic ointment, USP grade (70 grams) and the mixing continued until a uniform consistency is obtained.

EXAMPLE 21

A cream composition containing 15% N,N-dimethyloctamide and 2% hydroquinone is formulated as follows. N,N-Dimethyloctamide (15 grams) and hydroquinone (2 grams) are dissolved in propylene glycol (5 m)l. The solution thus prepared is mixed with hydrophilic ointment (80 grams) until a consistent cream is obtained.

EXAMPLE 22

A solution composition containing 10% hexamethylene palmitide, in oil-in-water emulsion is prepared as follows. Hexamethylene palmitide, (10 grams) is dissolved in propylene glycol (10 ml). The solution is then mixed with hydrophilic ointment, USP grade (80 grams) and the mixing continued until a uniform consistency is obtained.

EXAMPLE 23

To determine whether the base-containing compositions of Examples 4 through 22 or related compositions ("compositions") are therapeutically effective for alleviating or improving the signs of skin aging, patients and voluntary subjects (collectively "participants") are included in a study where the compositions are topically administered twice daily on the face and hands of the participants for a time period of 6 to 12 months. For optimal bioavailability, the compositions are formulated to contain 5 to 30%, and preferably between 8 to 20% of the active agent. For the duration of the study, the participants are instructed to avoid sun exposure, or if such is not possible, to use a sunscreen product with a sun protection factor of 15 or greater.

Prior to attending the study, each participant is requested to appear to the study without any make-up or concealers on their face or hands. At the beginning of the study, the quality of the participants skin is examined and documented. Skin characteristics that should be considered are texture (i.e., smooth, rough), translucency (glossy, dull), and touch (soft, coarse). In addition to the examination, four photographs are taken of each participant: one of each side of the face and one of the back of each hand. To take the photographs, the same light source and two foot distance is used to photograph the face and hands of each participant. For photographs of the face, the camera is aimed perpendicularly at a locus on the frontal aspect of each cheek. For photographs of the hands, the camera is aimed perpendicularly at the centermost part of the back of each hand.

For the duration of the study, participants are to return to the clinic conducting the study on a monthly basis for follow-up examinations and photographs. Participants are instructed to continue to not wear any make-up or concealers on their face and hands when appearing for their monthly photographs. During examination, the quality of the participants' skin is examined in order to see how the skin has reacted to the topical base, i.e., whether the skin has become smoother, glossier, or softer, or if the skin has become irritated. If a participant shows signs of irritation from the topical composition applied, such should be recorded, and a lower concentration of the same composition should be administered for the following month. If the participant continues to show signs of irritation with the lower concentration compositions, then a different composition should be administered to the patient until no more irritation is observed. All participants are instructed to notify the clinic immediately and to discontinue use of the compositions if the irritation becomes severe. Severe irritation will be a subjective determination but will always involve irritation causing extreme discomfort. Examples of severe irritation may include symptoms such as visible redness, itching, dryness, and flaking of the skin that continues without interruption for a period of ten days or more.

In addition to the foregoing, the appearance of the participants' skin on the face and on the back of the hands is compared to the previous months' photographs. The following signs of age are documented as being improved, as worsening, or as remaining the same: skin lines, fine wrinkles, coarse wrinkles, age spots, pigmented spots, brown spots, blotches, blemishes, and nodules.

EXAMPLE 24

Compositions containing a high concentration (50% or higher) to full-strength (100%) of the bases of Examples 4–22 or related compositions (compositions) may be used in an office procedure or treatment. The compositions are topically applied to the patient's skin by a dermatologist or a trained professional and, using rubber gloves, gently massaged in with the fingers or a cotton ball. The length of time of the massage will depend on the strength of the composition and the patient's skin sensitivity to the composition, but usually will be for one to a few minutes. After the massage, the patient's skin is gently rinsed with water.

For optimal effect, the office procedure should be repeated every two to three weeks. Photographs, as described in the previous example, should be taken of the patient's skin before the first application and repeated before every visit or before every second or third visit. Improvements should be seen after three to five office visits; however, with some patients, eight to twelve office visits may be necessary.

If so desired, the home treatment regime set forth in the prior example may be combined with the office procedure set forth herein to increase the therapeutic effects of the base-containing composition. Under this procedure, the patient is to apply the lower dose compositions set forth in Example 23 between office visits.

We claim:

1. A method of promoting keratolysis of skin comprising topically applying to an individual's skin in need thereof a formulation consisting essentially of a cosmeceutically active base at a concentration of between 0.3 to 7.0 weight percent, sufficient to provide a pH at the skin surface in the range of approximately 8.0 to 13.0, wherein the active base is NaOH.

2. The method of claim 1, wherein the pH is in the range of approximately 8.5 to 11.5.

3. The method of claim 2, wherein the pH is in the range of approximately 8.5 to 10.5.

4. The method of claim 1, wherein the formulation is aqueous.

5. The method of claim 4, wherein the aqueous formulation is selected from the group consisting of a cream, a gel, a lotion, and a paste.

6. The method of claim 5, wherein the aqueous formulation is a gel.

7. The method of claim 1, wherein the formulation is applied once daily.

8. The method of claim 1 wherein the concentration of base is 0.5 to 4.0 wt %.

9. The method of claim 8 wherein the concentration is 0.5 to 3.0 wt %.

10. The method of claim 9 wherein the concentration is 0.75 to 2.0 wt %.

11. The method of claim 5 wherein the concentration is 0.75 to 2.0 wt %.

* * * * *